US005782917A

United States Patent [19]
Carn

[11] Patent Number: 5,782,917
[45] Date of Patent: Jul. 21, 1998

[54] INTRAMEDULLARY BONE PLUG

[75] Inventor: Ronald M. Carn, Redding, Calif.

[73] Assignee: Sunmed, Inc., Redding, Calif.

[21] Appl. No.: 756,944

[22] Filed: Dec. 2, 1996

Related U.S. Application Data

[62] Division of Ser. No. 607,242, Feb. 26, 1996.
[51] Int. Cl.$^6$ .................................................. A61F 2/28
[52] U.S. Cl. ............................ 623/16; 606/62; 606/95
[58] Field of Search .......................... 623/16, 23, 18; 606/60–62, 92–95, 89

[56] References Cited

U.S. PATENT DOCUMENTS

| | | | |
|---|---|---|---|
| 4,245,359 | 1/1981 | Stuhmer | 606/95 |
| 4,293,962 | 10/1981 | Fuson | 606/95 |
| 4,302,855 | 12/1981 | Swanson | 606/95 |
| 4,447,915 | 5/1984 | Weber | 606/95 |
| 4,697,584 | 10/1987 | Haynes | 606/95 |
| 5,078,746 | 1/1992 | Garner | 606/95 |
| 5,100,405 | 3/1992 | McLaren | 606/72 |

FOREIGN PATENT DOCUMENTS

| | | | |
|---|---|---|---|
| 6408 | 1/1980 | European Pat. Off. | 606/95 |
| 4136317 | 5/1993 | Germany | 606/95 |

*Primary Examiner*—Robert A. Clarke
*Assistant Examiner*—Bruce E. Snow
*Attorney, Agent, or Firm*—Kelly, Bauersfeld Lowry & Kelley, LLP

[57] ABSTRACT

A bone plug is provided for insertion into the medullary canal of a patient bone during orthopedic surgery, wherein the bone plug restricts or prevents passage of bone cement introduced under pressure into the medullary canal. The bone plug comprises a generally cylindrical member formed from a biocompatible material such as polyethylene and having sets of distal and proximal fins. The distal fins are defined by a spiral thread set at an angle to extend distally, to bend to accommodate the shape of the medullary canal and thereby anchor the bone plug by biting into patient bone, whereas the proximal fins flex during plug insertion to extend proximally and thereby seal against bypass flow of bone cement past the bone plug. An insertion tool is also disclosed, for use in placing the bone plug during a surgical procedure, such as hip arthroplasty.

2 Claims, 4 Drawing Sheets

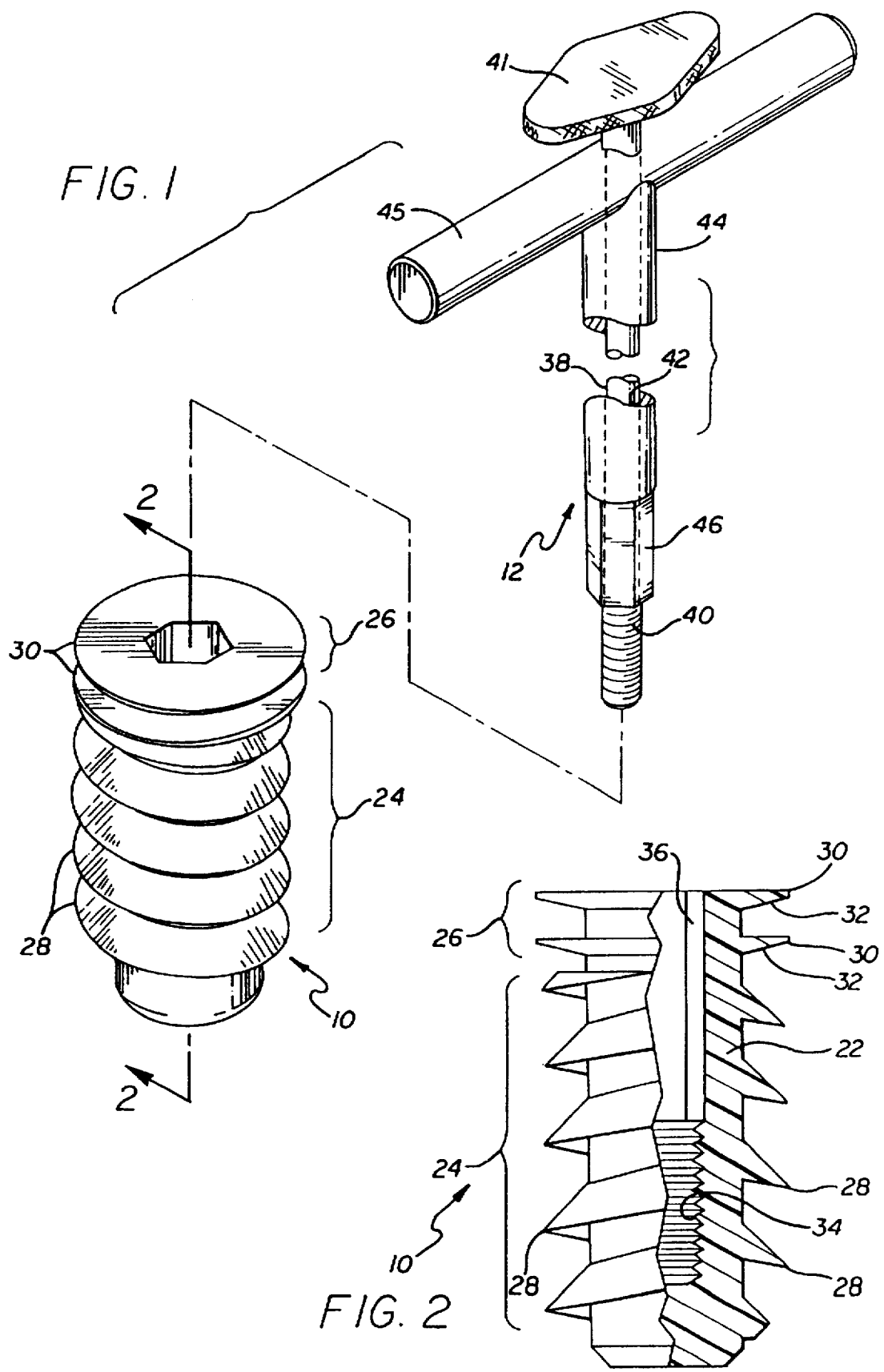

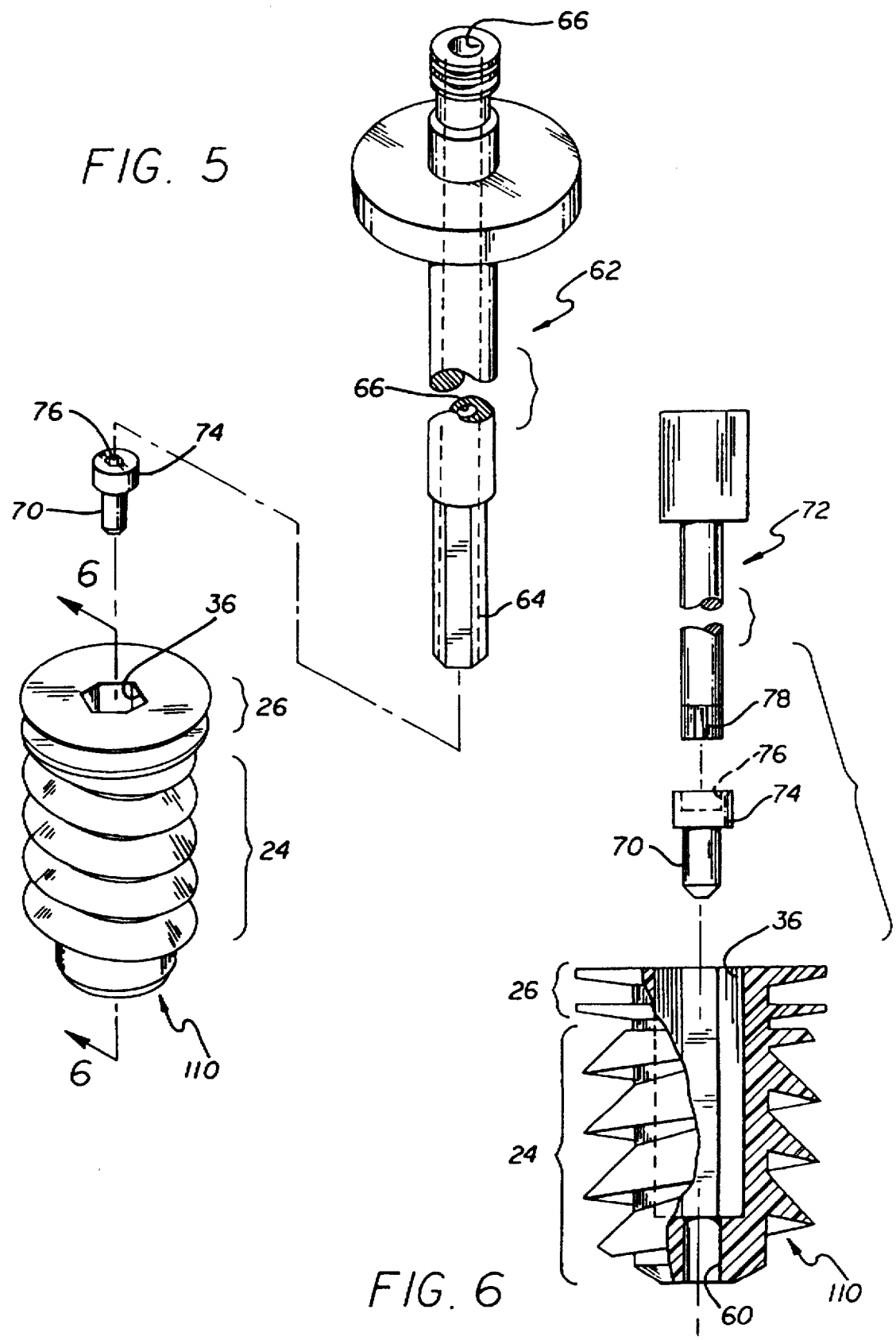

INTRAMEDULLARY BONE PLUG

This is a division of application Ser. No. 08/607,242, filed Feb. 26, 1996.

BACKGROUND OF THE INVENTION

This invention relates generally to improvements in devices and procedures for artificial joint replacement (arthroplasty). More specifically, this invention relates to an improved intramedullary bone plug for confining or restricting the placement of bone cement introduced under pressure into the medullary canal of a patient bone during arthroplasty surgery, such as a hip joint replacement.

Artificial or prosthetic joint structures are used extensively to repair or replace a patient joint, particularly such as hip, knee and shoulder joints. The prosthesis typically comprises a biocompatible structure or structures formed from cobalt-chrome alloy with a size and shape for secure affixation to a surgically resected patient bone. In many cases, the prosthetic device includes an elongated stem for slide-fit placement into the exposed medullary canal of a resected patient bone, such as the upper end of a patient's femur in the case of a hip replacement. A bone cement, typically methyl methacrylate, is often introduced under pressure into the medullary canal to provide a positive and stable prosthesis attachment to the patient bone. The pressurized bone cement is intended to fill the interstices of the bone structure in surrounding relation to the prosthetic device to result in optimal prosthesis fixation.

When pressurized bone cement is introduced into the medullary canal, it is necessary or desirable to use a restrictor or plug element to confine the cement to surrounding relation with the prosthesis, rather than to permit the bone cement to travel distally through the medullary canal in a direction away from the prosthesis. In this regard, numerous restrictor or plug devices have been developed for this purpose, and are adapted to be installed into the medullary canal immediately prior to placement of the prosthesis and bone cement. However, such prior restrictor or plug devices have not functioned in a fully satisfactory manner. To the contrary, such prior restrictor or plug devices have suffered from bypass leakage of the bone cement, or alternately from undesired sliding movement in a distal direction when subjected to bone cement under pressure. Either problem results in inadequate pressurization of the cement and corresponding less-than-optional fixation of the prosthesis.

There exists, therefore, a significant need for an improved bone plug for use in orthopedic surgery, wherein the bone plug is securely anchored within the medullary canal and further provides a high quality seal to prevent bypass leakage of cement. The present invention fulfills these needs and provides further related advantages.

SUMMARY OF THE INVENTION

In accordance with the invention, an improved intramedullary bone plug is provided for controlling the placement of pressurized bone cement into the medullary canal of a patient bone during orthopedic surgery such as hip replacement surgery. The improved bone plug includes a generally cylindrical body in combination with distal fins and proximal fins which function respectively to anchor the plug within the patient bone and to prevent bypass leakage of pressurized bone cement in a distal direction past the plug.

The improved bone plug is formed from a biocompatible material such as polyethylene or the like and preferably has a one-piece construction to include the distal and proximal fins formed integrally on the plug body. The distal fins comprise a spiral thread which is angularly set to define a sharp leading edge presented in a downstream or distal direction to bite or anchor securely into the patient bone defining the medullary canal. By contrast, the proximal fins are formed to extend radially on the plug body, but have sufficient resilience so that the outer edges thereof deflect proximally when the bone plug is installed. The proximal fins thus act to engage and seal with the patient bone to prevent bone cement bypass leakage, while the distal fins positively secure the bone plug against distal slippage when the pressurized bone cement is introduced into the medullary canal. The threads are also used to advance the device in a screwlike fashion to the desired location in the medullary canal. The undercut nature of the thread design allows the threads to bend and accommodate the irregularities of the medullary space.

An insertion tool is also provided for quickly and easily installing the bone plug. The insertion tool comprises an elongated stylet having a threaded tip for thread-in engagement with a threaded socket formed in the proximal end of the plug body. This threaded socket is disposed distally relative to a hex socket in the plug body for receiving a hex head tip on a driver. In the preferred form, the driver is constructed as a hollow sleeve member for slide-fit reception of the stylet and threaded tip thereon. Accordingly, the stylet and driver can be manipulated independently to position and lockingly set the bone plug. An alternative design may utilize a longer hex socket without the threaded portion, to allow for the placement tool to be a single component but wherein a separate tool would be needed for plug extraction.

In an alternative embodiment of the invention, the bone plug can be formed to define the hex socket in the plug body to receive the hex head tip of the driver, but wherein a distal end of the hex socket communicates with a through port that enables body fluids and the like to escape through the bone plug as the plug is installed. A suitable suction instrument may be employed to remove accumulated fluids and the like disposed proximally of the installed bone plug. A stopper pin is provided for seated placement into the through port to close said port prior to introduction of bone cement into the medullary canal.

Further aspects and features of the improved intramedullary bone plug of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating the improved intramedullary bone plug and related installation tool embodying the novel features of the invention;

FIG. 2 is a side elevation view, shown partly in vertical section, of the bone plug;

FIG. 5 is an exploded perspective view illustrating an alternative embodiment of the bone plug and related installation tool;

FIG. 6 is an exploded and fragmented sectional view taken generally on the line 6—6 of FIG. 5;

DETAILED DESCRIPTION OF THE PREFERRED EMBODIMENT

Figures 3, 4:
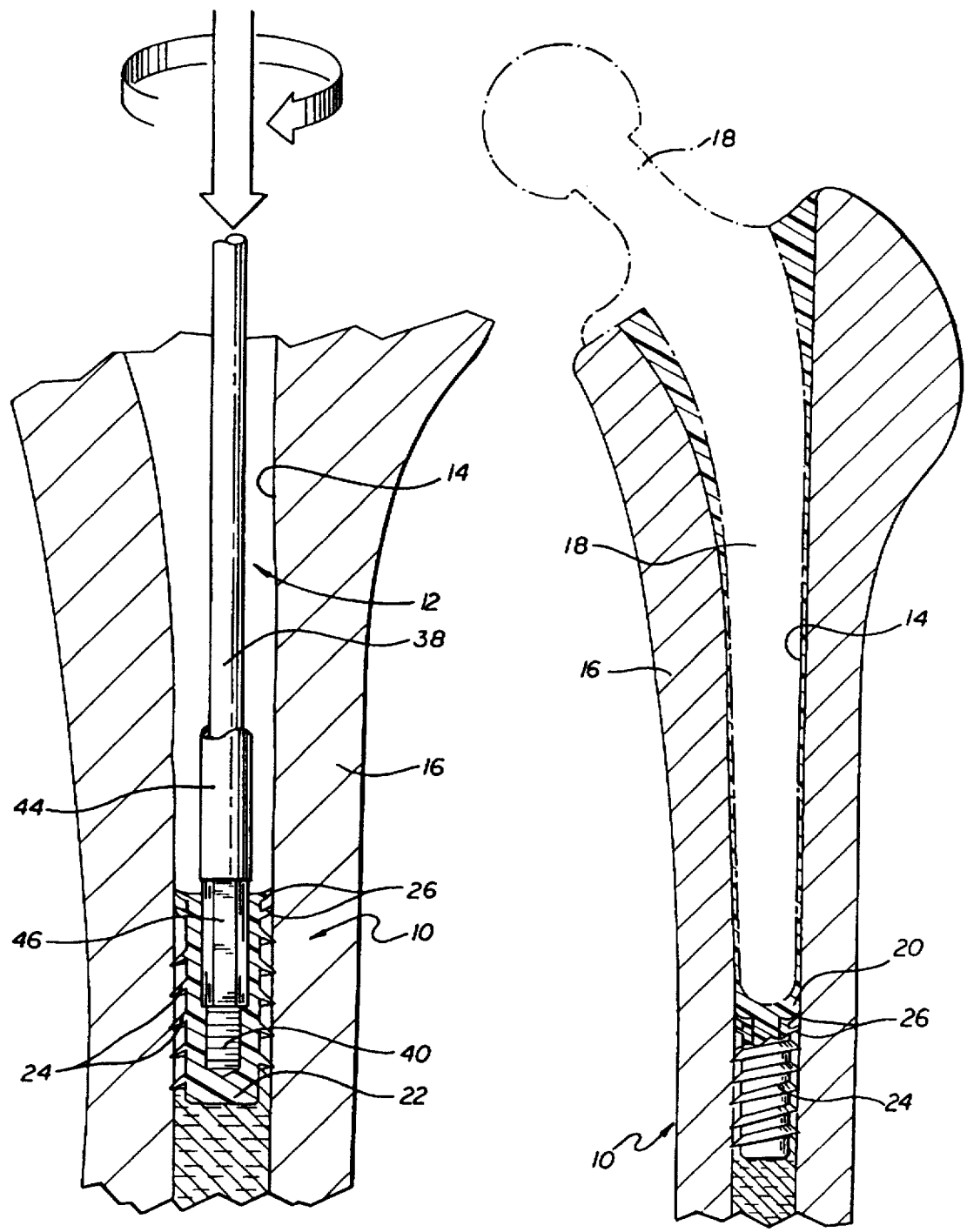
FIG. 3 is a fragmented sectional view depicting use of the installation tool to place the bone plug in the medullary canal of a resected femur.
FIG. 4 is a fragmented sectional view showing the bone plug in relation to an installed hip prosthesis.

As shown in the exemplary drawings, an improved intramedullary bone plug is referred to generally by the reference numeral 10. The bone plug 10 is designed for placement into the medullary canal of a patient bone, by means of an insertion tool 12.

As shown best in FIGS. 3 and 4, the bone plug 10 of the present invention is positioned within the medullary canal 14 of a patient bone, such as a resected femur 16 in the case of hip replacement surgery, at a location spaced slightly downstream or distally from an associated prosthesis 18 (FIG. 4). In use, the bone plug provides a barrier to block and retain bone cement 20 introduced under pressure into the medullary canal 14. The bone plug 10 thus confines the bone cement to the space surrounding the prosthesis 18, to achieve substantially optimum prosthesis fixation.

The bone plug 10 is formed from a suitable biocompatible material such as polyethylene or the like, and preferably is a one-piece component. The plug comprises a generally cylindrical body 22 (FIG. 2), in combination with a set of distally positioned fins 24 and another set of proximally positioned fins 26. The diametric size of the plug body 22 with the sets of fins 24, 26 is chosen to fit into the medullary canal 14, with the fins 24, 26 engaging the patient bone lining the canal as will be described in more detail. In this regard, the bone plug 10 of the present invention is particularly configured to fit into a medullary canal of approximately uniform cross sectional size. For the construction and functional operation of a related bone plug configured for use with a medullary canal of nonuniform cross sectional size, see copending U.S. Ser. No. 08/587,491, filed Jan. 17, 1996.

The distal fins 24 are formed as a spiral thread with multiple turns, with the illustrative drawings showing 4–5 turns. This spiral thread is angled or canted in a distal direction to define a leading and relatively sharp outer edge 28 presented distally. With this geometry, the distal fins 24 are configured to engage or bite into the patent bone lining the medullary canal, and thereby positively lock and anchor the plug 10 against downstream sliding motion. The unique thread design with an undercut configuration allows the threads to bend or conform to the shape of the medullary canal yet still provide a sharp outer edge to engage the medullary bone.

The proximal fins 26 are formed as multiple annular rings, shown as a pair, having outer edges 30 for engaging the patient bone. As shown, these annular fin rings 26 have angled distal faces 32 to facilitate flexing of the fins 26 as the plug 10 is installed. As a result, the outer edges 30 of the proximal fins 26 re-orient to extend in an upstream or proximal direction where they function as seals to prevent bypass leakage of bone cement.

The bone plug 10 further includes a threaded socket 34 formed therein in combination with a hex socket 36 disposed between the threaded socket 34 and an open proximal end of the plug. These sockets 34, 36 are adapted to receive the installation tool 12 for retaining and manipulating the plug during intramedullary placement. The preferred installation tool includes an elongated stylet 38 with a threaded tip 40 at one end thereof and a handle 41 at an opposite end. The tip 40 is adapted for thread-in engagement with the threaded socket 34. The stylet 38 is sized to slide-fit through a bore 42 in a driver 44 having a hex head 46 for engaging the hex socket 36. The driver 44 also includes a handle member 45 opposite the hex head.

In use, the stylet 38 is assembled with the driver 44 as shown in FIGS. 1 and 3, with the threaded tip 40 and the hex head 46 engaging the plug body. The plug can then be manipulated with ease to install the plug into the medullary canal 14. The driver 44 can be rotated as needed to advance the plug to the desired position. The lengths of the stylet and driver can be used as a gauge for proper plug placement. The driver 44 and stylet 38 can then be separated from the installed plug 10, leaving the plug in place as a barrier to block the bone cement 20 (FIG. 4) introduced subsequently under pressure. The distal fins 34 positively anchor the plug 10 against pressure-caused distal displacement, while the proximal fins 36 seal against bypass leakage of the bore cement.

Figures 7, 8:
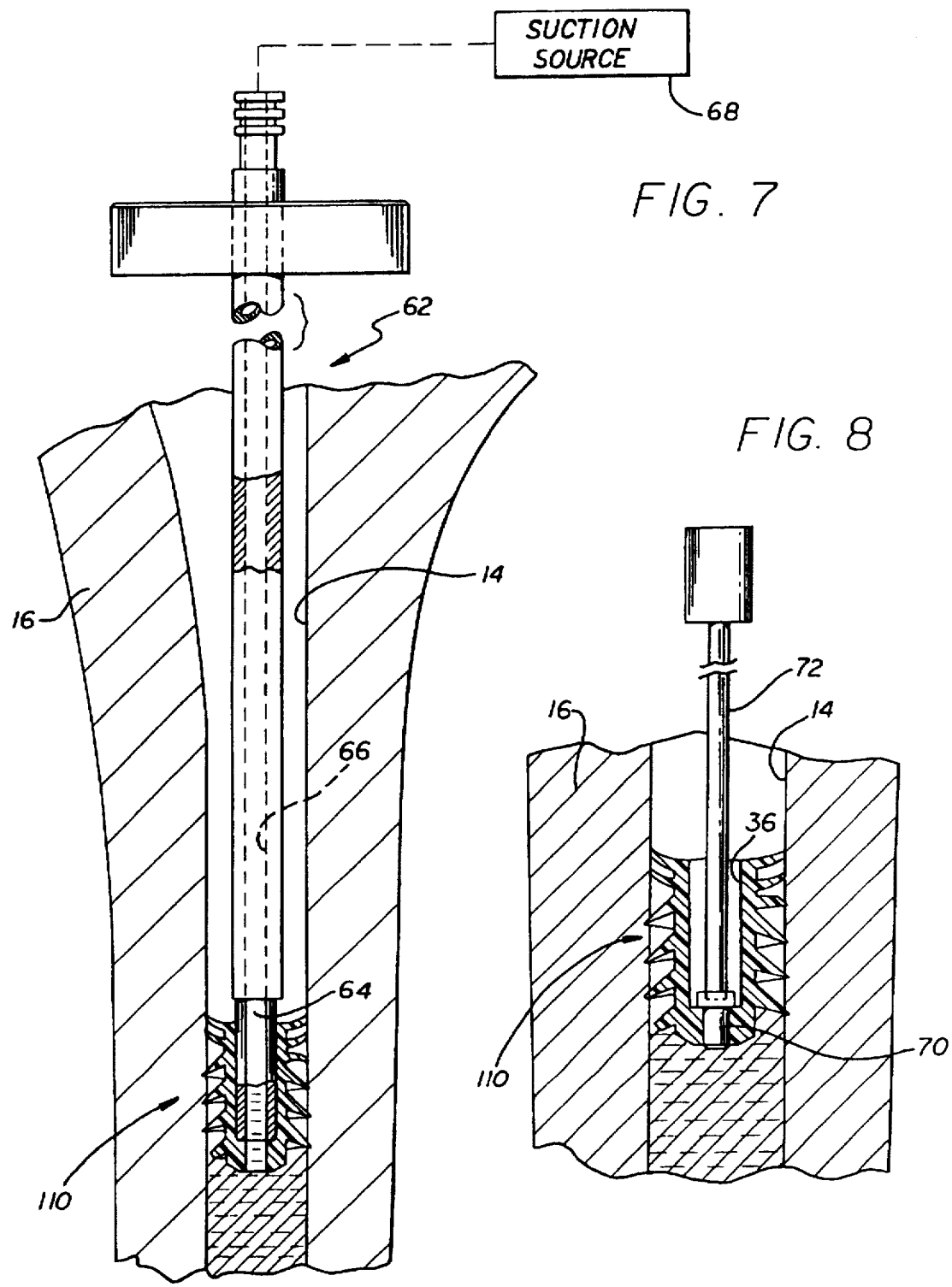
FIG. 7 is a fragmented sectional view showing installation of the bone plug of FIGS. 5 and 6 into the femur.
FIG. 8 is a fragmented sectional view similar to FIG. 7, and showing placement of a stopper pin into the bone plug.

FIGS. 5–8 illustrate an alternative preferred form of invention, wherein a modified bone plug 110 is generally constructed according to FIGS. 1–4 to include the distal fins 24 and proximal fins 26, but further wherein the internal hex socket 36 communicates with an open through port 60 at the distal end of the bone plug. As shown in FIG. 7, the bone plug 110 is initially installed into the medullary canal 14 of the femoral bone 16 or the like by means of a driver 62 having a head 64 for reception into the hex socket 36 of the bone plug. During this installation step, the driver 62 can be appropriately rotated to seat the bone plug distal end proximal fins 24, 26, as previously described, while the distal through port 60 permits body fluids and the like located distally of the bone plug 110 to escape to the proximal side thereof where they can be removed by coupling a cannula passage 66 through the driver 62 to an appropriate suction source 68 (FIG. 7). Thereafter, the driver 62 can be used as the guide to slide the stopper pin 70 into the seated position within the port 60. An alterative is that the driver 62 can be removed and a stopper pin 70 seated within the through port 60 by means of an insertion tool 72. As shown, the stopper pin 70 has an enlarged head to seat within the bone plug 110 at the proximal end of the port 60, with a hex socket 76 in the head 74 permitting convenient engagement with a hex tip 78 on the insertion tool. After the stopper pin 70 is placed, as viewed in FIG. 4, the prosthesis can be installed with appropriate application of bone cement under pressure, with the bone plug 110 and associated stopper pin 70 preventing bypass flow of the cement past the bone plug.

A variety of further modifications and improvements to the bone plug 10 of the present invention will be apparent to those skilled in the art. Accordingly, no limitation on the invention is intended by way of the foregoing description and accompanying drawings, except as set forth in the appended claims.

What is claimed is:

1. A method of installing an intramedullary bone plug into the medullary canal of a patient bone, said method comprising the steps of:

placing the bone plug with an insertion tool at a selected position within the medullary canal of the patient bone;

suctioning body fluid disposed distally of the bone plug within the medullary canal through a suction port formed in the bone plug; and closing the suction port with a stopper pin.

2. The method of claim 1 wherein said suctioning step comprises suctioning the body fluid through the bone plug suction port and further through a cannula passage formed in the installation tool.

* * * * *